United States Patent [19]
Geerts et al.

[11] 3,954,771
[45] May 4, 1976

[54] PROCESS FOR THE PREPARATION OF 2H-3-ISOQUINOLONES

[75] Inventors: Jean-Pierre Jules Geerts; Raymond Armand Linz, both of Brussels, Belgium

[73] Assignee: UCB, Societe Anonyme, Saint-Gilles-lez-Bruxelles, Belgium

[22] Filed: May 31, 1973

[21] Appl. No.: 365,723

[30] Foreign Application Priority Data
June 16, 1972 United Kingdom............... 28226/72

[52] U.S. Cl........................ 260/283 SY; 260/289 D
[51] Int. Cl.²................................. C07D 217/32
[58] Field of Search....... 260/283 SY, 289 R, 289 D

[56] References Cited
UNITED STATES PATENTS

| | | | |
|---|---|---|---|
| 2,759,936 | 8/1956 | Skeeter.......................... | 260/283 SY |
| 3,457,266 | 7/1969 | Gibas............................ | 260/283 SY |

OTHER PUBLICATIONS
Haworth, J. Chem. Soc. (1927) pp. 2281–2284.

*Primary Examiner*—R. Gallagher
*Assistant Examiner*—D. B. Springer
*Attorney, Agent, or Firm*—Wenderoth, Lind & Ponack

[57] ABSTRACT

A process for the preparation of 2H-3-isoquinolones having the formula

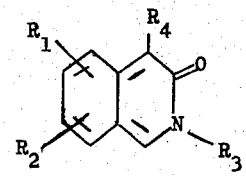

wherein $R_1$ and $R_2$ are each hydrogen, halogen, lower alkyl, lower alkoxy, aryl, haloaryl, alkylaryl or alkoxyaryl; $R_3$ and $R_4$ are each hydrogen, lower alkyl, lower alkoxyalkyl, lower alkenyl, lower alkynyl, cycloalkyl, aryl, aralkyl, or halo-aralkyl, which comprises cyclizing an N-formyl-2-phenyl-acetamide of the formula

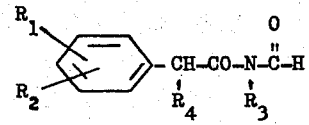

wherein $R_1$, $R_2$, $R_3$ and $R_4$ have the same meaning as above, with a cyclodehydration agent. Said 2H-3-isoquinolones are useful as starting materials e.g. in the synthesis of 1,4-dihydro-1,4-etheno-isoquinolin-3(2H)-ones which are valuable chemotherapeutic agents in the treatment of disorders of the central nervous system, such as troubles of wakefulness, disorders of equilibrium and vertigo.

14 Claims, No Drawings

PROCESS FOR THE PREPARATION OF 2H-3-ISOQUINOLONES

The present invention is concerned with the preparation of 2H-3-isoquinolones by a new and advantageous process, as well as with the 2H-3-isoquinolones obtained by this new process, most of which are new. It is also concerned with these new compounds.

2H-3-isoquinolones are valuable intermediates for the preparation of pharmaceutical products, dyestuffs, antioxidants and photographic materials.

Thus, for example, the 2H-3-isoquinolones obtained by the process of the present invention are used as starting materials in the production of 1,4-dihydro-1,4-etheno-isoquinolin-3(2H)-ones according to the process disclosed in copending U.S. Application Ser. No. 352,239 entitled "A process for the preparation of 1,4-dihydro-1,4-etheno-isoquinolin-3(2H)-ones-" filed on or about Apr. 18, 1973 in the name of René Denayer, which is a continuation-in-part of copending application Ser. No. 191,064, filed on Oct. 20, 1971, now abandoned (see also Belgian Patent Specification No. 774,240). The usefulness of these 1,4-dihydro-1,4-etheno-isoquinolin-3(2H)-ones as chemotherapeutic agents valuable in the treatment of disorders of the central nervous system, i.e. troubles of wakefulness, disorders of equilibrium and vertigo, psychosomatic disorders, neuroses, disorders due partcularly to senility, delirous and hallucinatory psychoses and as an antalgic, is disclosed in copending U.S. application Ser. No. 191,063 (U.S. Pat No. 3,781,436) entitled "Therapeutic compostions" filed on Oct. 20, 1971 in the name of Corneliu Edmond Giurgea (see also Belgian Patent Specification No. 774,241).

The 2H-3-isoquinolones were hitherto not readily available as starting materials, because the known methods do not enable them to be prepared in a simple and economic manner.

One of the known methods (see F. Johnson and W. A. Nasutavicus, J.Org.Chem.,27,(1962),3953) starts from homophthalonitrile (R = H) and gives 3-aminoisoquinoline (3) which may subsequently be converted into 2H-3-isoquinolone (4) by means of nitrous acid (see H. E. Baumgarten et al. J.Org.-Chem.,26,(1961),803), the yield obtained being 53 to 65%.

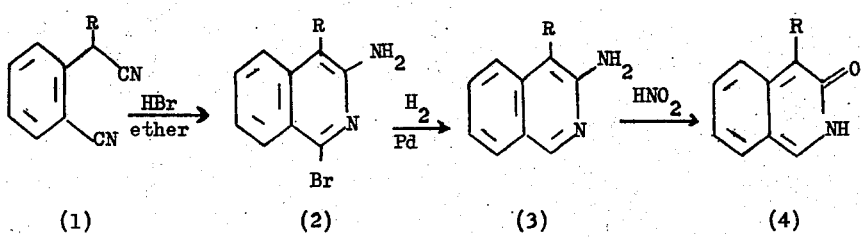

The route from 1 to 4 gives an overall yield of 37%.

However, the homophthalonitrile used as starting material is an expensive material which is prepared from o-toluidine by diazotization and Sandmeyer reaction followed by bromination and elongation of the chain by sodium cyanide, the overall yield being 35%;

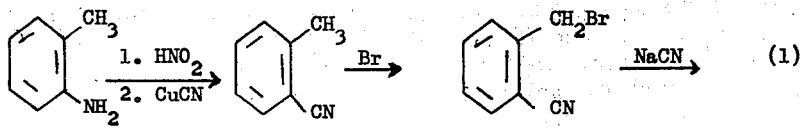

For this reason, the yield of isoquinolone, starting from o-toluidine, is consequently only 10.5 to 13%.

Furthermore, obtaining derivatives which are substituted in the benzene nucleus is difficult and the yields obtained are very low.

T. Okano, S. Goya and J. Tsuda (Yakugaku Zasshi,86,(1966),544) started from phthalide, which is also an expensive material. They carried out the synthesis of 3-aminoisoquinoline (6) by the following five stages; the final yield of 2H-3-isoquinolone is 9.5 to 11.7%:

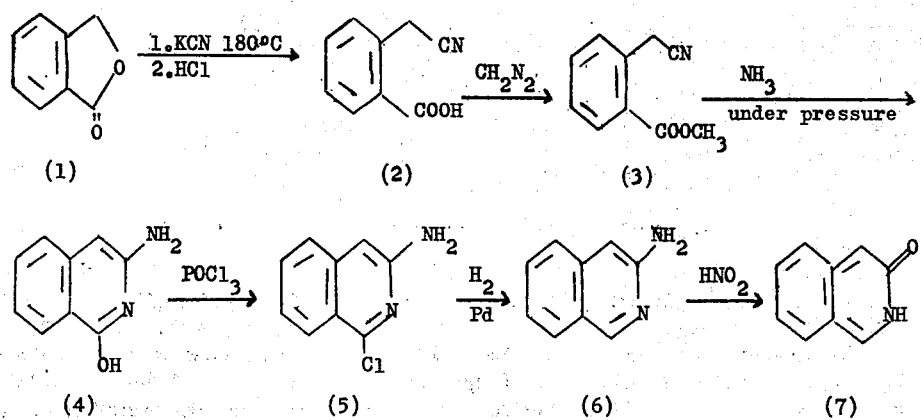

D. W. Jones (J.Chem.Soc.1969,1729) started from methyl 2-formylphenyl-acetate and ammonia:

methylisoquinoline (1) for a five-stage synthesis of 3-amino-isoquinoline (6), the overall yield being 28%:

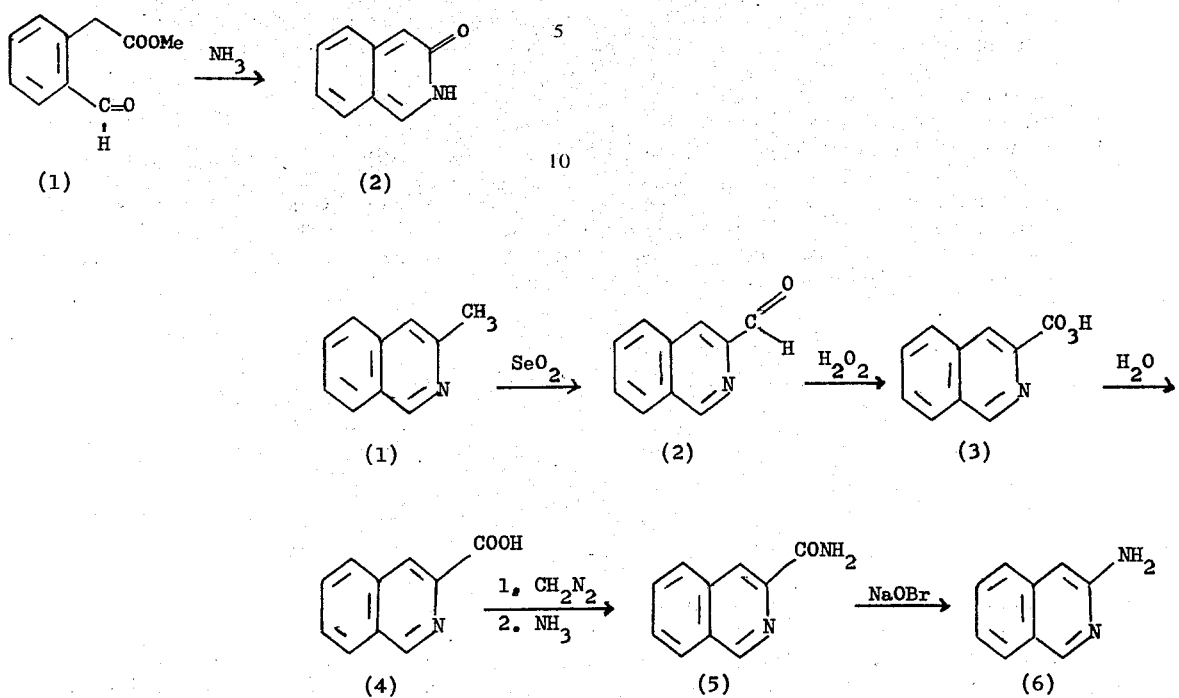

However, compound (1) is difficult to obtain.

Six stages of reaction are required and the starting material, ethyl phenylene-bis-1,2-diacetate (3) is itself a difficulty available substance:

Although the transformation of the amino-isoquinoline (6) into isoquinolone proceeds with a yield of 53 to 65%, the overall yield is only 14.8 to 17.6%.

Finally, N. J. Mc Corkindale and A. W. Mc Culloch

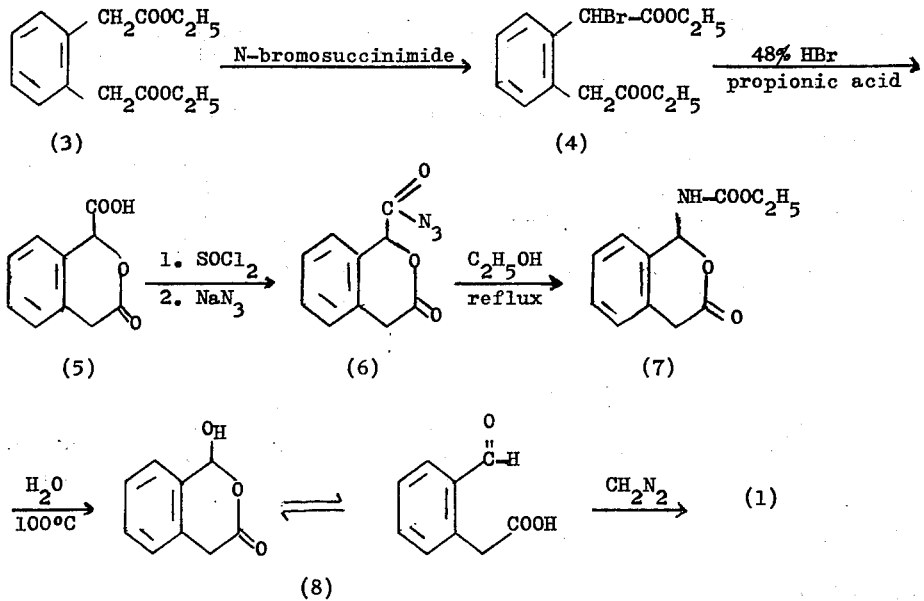

The overall yield, starting from (3), reaches 14.5% of product (2).

H. E. Baumgarten and J. E. Dirks (J.Org.- Chem.23,(1958),900), as well as C. E. Teague and A. Roe (J.A.C.S.,73,(1951),688), started from 3-

(Tetrahedron,27, (1971),4653) have been able to synthesize, in four stages, 2H-3-isoquinolone substituted by methoxy radicals in the benzene nucleus, starting from 4,5-dimethoxy-2-chloromethyl-phenyl-acetic acid, but the overall yield is only 13.3%:

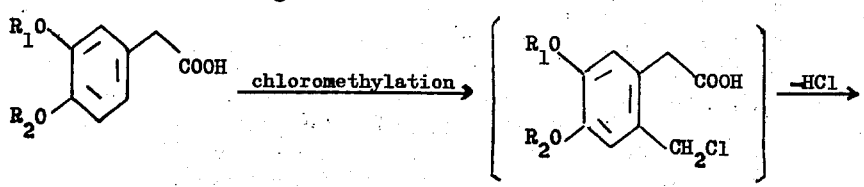

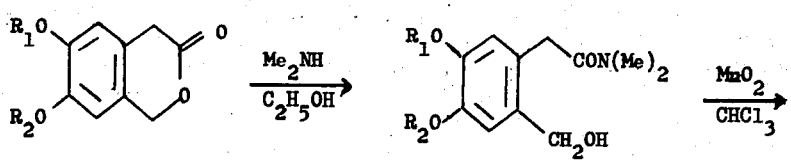

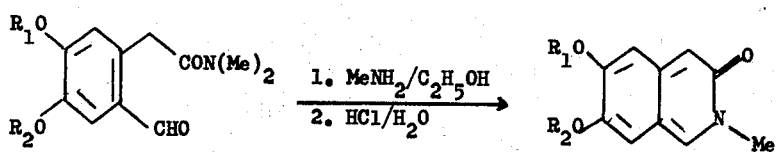

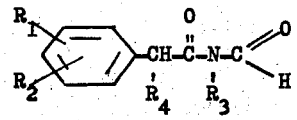

From the foregoing, the following is to be pointed out:

a. up until now no general method exists for the preparation of both substituted and unsubstituted 2H-3-isoquinolones;
b. the starting materials are expensive and difficult to obtain;
c. the yields are of the order of 9 to 18% and the number of steps is at least 4;
d. for obtaining derivatives substituted in the benzene nucleus, the yields are generally extremely low.

Consequently, there is interest in discovering a process for the synthesis of 2H-3-isoquinolones which is simple, permitting the preparation of unsubstituted as well as of substituted compounds, starting from materials which are not very expensive and giving good yields.

Thus, according to the present invention, there is provided a process for the synthesis of 2H-3-isoquinolones of the general formula:

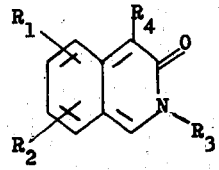

(I)

wherein $R_1$ and $R_2$, which may be the same or different, are hydrogen or halogen atoms, alkyl or alkoxy radicals containing up to 6 carbon atoms or unsubstituted or substituted aryl radicals; and $R_3$ and $R_4$, which may be the same or different, are hydrogen atoms or unsubstituted or substituted alkyl, alkenyl, alkynyl, cycloalkyl, aryl or aralkyl radicals, characterized in that N-formyl-2-phenyl-acetamides of the general formula:

$$R_1 \diagup\!\!\!\!\diagup\!\!\!\!\diagdown \text{—CH—C—N—C} \diagup\!\!\diagdown^{O}_{H} \quad (II)$$
$$R_2 \qquad\qquad R_4 \; R_3$$

wherein $R_1$, $R_2$, $R_3$ and $R_4$ have the same meanings as above, are cyclized with a cyclodehydration agent to give an isoquinolone salt which, if desired, is treated in known manner with a basic substance to give the free isoquinolone.

In general formulae (I) and (II) above, $R_1$ and $R_2$ each represent a hydrogen atom or a halogen atom, such as a fluorine, bromine, or preferably, chlorine atom, an alkyl or alkoxy radical containing up to 6 carbon atoms, for example a methyl, methoxy, ethyl, ethoxy, propyl, propoxy, isopropyl, isopropoxy, n-butyl, n-butoxy or like radical, or an aryl radical, such as a phenyl or naphthyl radical, which may also contain at least one substituent, for example, a halogen atom, such as a fluorine, chlorine or bromine atom, a lower alkyl radical, such as a methyl, ethyl, propyl or like radical or a lower alkoxy radical, such as a methoxy, ethoxy, propoxy or like radical.

The radicals $R_3$ and $R_4$ in the above-given general formulae (I) and (II) each represent a hydrogen atom, an alkyl radical containing up to 6 carbon atoms, such as a methyl, ethyl, propyl, n-butyl or like radical, a lower alkyl radical which may be substituted for example by a lower alkoxy group (e.g. methoxymethyl or like radical), an alkenyl radical containing 2 to 6 carbon atoms, such as an ethenyl, allyl or like radical, an alkynyl radical containing 2 to 6 carbon atoms, such as a propargyl or like radical, a cycloalkyl radical containing 3 to 6 carbon atoms, such as a cyclopentyl, cyclohexyl or like radical, an aryl radical, such as a phenyl, naphthyl, tolyl, xylyl or like radical, or an aryl-lower alkyl radical, such as a benzyl, phenethyl or like radical, which may be substituted e.g. by a halogen, such as p-chlorophenethyl or like radical.

The cyclodehydration agent is preferably an inorganic acid such as sulfuric, phosphoric and polyphosphoric acids, an anhydrous hydrohalogenic acid preferably in an acetic acid medium, or the like. However other agents may also be used such as acetic anhydride, p-toluenesulfonic acid, sulfur trioxide, phosphorus pentoxide, a mixture of sulfur dioxide and phosphorus pentoxide, phosphorus oxychloride, aluminium chloride, alumina and the like. The preferred cyclodehydration agent is sulfuric acid.

According to the present invention, for the cyclodehydration of the N-formyl-2-phenyl-acetamides of general formula (II) to give 2H-3-isoquinolones of general formula (I), a compound of general formula (II) is dissolved in the cyclodehydration agent, while stirring and maintaining a temperature between 0° and 60°C., whereafter the reaction mixture is left to stand for a period of 1 to 48 hours.

Then, according to one method, the reaction mixture is diluted with water and neutralized with an excess of a basic agent, such as sodium bicarbonate or ammonium hydroxide. The reaction product may be separated by filtration or by extraction by means of a solvent, such as chloroform, methylene chloride or n-butanol. According to another method of separation, the reaction medium, without dilution, is poured directly, at a temperature below 50°C., into a suspension of sodium bicarbonate in a solvent, such as chloroform, methylene chloride or the like. In this case, the inorganic salts, for example sodium sulfate and excess sodium bicarbonate, are separated by filtration and the filtrate is evaporated in order to isolate the 3(2H)-isoquinolones formed. These are generally compounds which crystallize well and have a sharp melting point.

However, the 2H-3-isoquinolones of general formula (I) may also be isolated in the form of well crystalline acid addition salts, for example as sulfates, either by pouring the acidic reaction mixture directly into ethanol, in which the salts crystallize, or by diluting with water and only partially neutralizing (pH 4) with a basic agent, such as sodium hydroxide, sodium carbonate or bicarbonate, ammonium hydroxide or the like, and separating the isoquinolone sulfate by filtration.

Some of the N-formyl-phenyl-acetamides of general formula (II) used as starting materials for the synthesis of the isoquinolones of general formula (I), such as for example N-formyl-2-phenyl-acetamide, are known compounds.

On the other hand, other phenyl-acetamides of general formula (II), such as N-formyl-N-methyl-2-phenyl-acetamide or the phenyl-acetamides substituted in the benzene nucleus, are new compounds; however, they may easily be prepared in good yields by the reaction of appropriately substituted phenyl-acetyl halides with optionally substituted formamides according to the following equation:

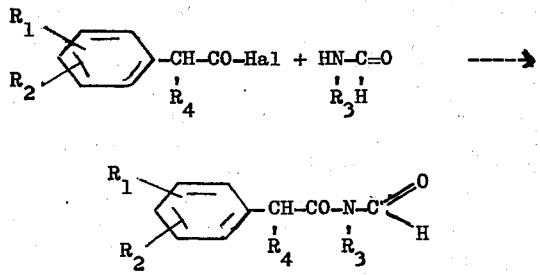

wherein Hal is a halogen atom and $R_1$ to $R_4$ have the same meanings as above, in the presence of an acid-binding agent, for example pyridine, and optionally of a suitable inert solvent, such as acetone, benzene, toluene or the like.

The advantages of the new process according to the present invention in comparison with the previously known processes for the preparation of 2H-3-isoquinolones are numerous:

a. it permits the preparation not only of 2H-3-isoquinolones, which may or may not be substituted on the nitrogen atom or in the 4-position of the isoquinoline nucleus, but also of 2H-3-isoquinolones which are substituted in the benzene nucleus;

b. the yields obtained are considerably higher;

c. the starting materials are obtained from readily obtainable compounds which are relatively inexpensive, namely, phenyl-acetic acids and optionally substituted formamides;

d. the process of the present invention is carried out in only two stages: synthesis of the N-formyl-phenyl-acetamides of general formula (II) starting from appropriate phenyl-acetic acids and formamides, then cyclodehydration of the compounds of general formula (II) to give 2H-3-isoquinolones of general formula (I), whereas the known processes are very laborious and require at least 4 operational stages;

e. the operational conditions of the process according to the present invention are very mild and do not involve the use of expensive reactants and solvents.

The following Examples are given for the purpose of illustrating the present invention:

EXAMPLE 1

Preparation of 2H-3-isoquinolone (known compound)

200 g. N-formyl-2-phenyl-acetamide are dissolved in an inert atmosphere (nitrogen) in 1250 ml. concentrated sulfuric acid, while stirring and cooling in a bath of cold water in order to maintain the temperature at about 20°–25°C., whereafter the reaction mixture is left to stand for 4 hours at ambient temperature. The sulfuric acid solution is then poured, with stirring, into about 4 liters of a mixture of ice and water, the temperature not exceeding 50°C. The reaction mixture is then filtered through "Hyflo Super-Cel" a very pure diatomaceous silica filter-aid sold by Johns-Manville Sales Corp. (HYFLO is a Trade Mark). The filtrate obtained is poured, while stirring mechanically and cooling in ice (temperature of the reaction medium about 20°C.), into 3.5 liters concentrated ammonium hydroxide solution. The yellow precipitate of 2H-3-isoquinolone obtained is filtered off, washed with water and dried. There are obtained 72 g. of product; m.p. 201°C.; yield 40% of theory.

However, the product can also be isolated in the form of the sulfate by proceeding in the following manner: after having diluted the sulfuric acid reaction medium with 2 volumes of water, there is added, while stirring and without exceeding a temperature of 40°C., 2.25 liters of concentrated ammonium hydroxide solution (final pH 4). There is formed a yellow precipitate of the sulfate of 2H-3-isoquinolone, which is filtered off, washed with water and dried. There are obtained 99 g. of product; m.p. 243°–245°C.; yield 40% of theory. The analysis shows that it is a compound of the empirical formula $(C_9H_7NO)_2 \cdot H_2SO_4 \cdot H_2O$:

analysis: calc. : C 53.9%; H 4.41%; N 6.72%; S 7.75%; $H_2O$ 4.37%; found : C 53.2%; H 4.43%; N 6.80%; S 7.87%; $H_2O$ 4.43%.

Starting from this sulfate, the free isoquinolone may be isolated by treating for example, a suspension of 10 g. of this sulfate in 100 ml. water with 10 g. sodium bicarbonate or 10 ml. ammonium hydroxide solution. The liberated isoquinolone is filtered off, washed with water and dried; m.p. 203°C.

N-formyl-2-phenyl-acetamide is a known compound (cf. H. Finkbeiner, J.Org.Chem.30,(1965),2861). It may also be easily prepared by reacting phenacetyl chloride with formamide according to the process described hereinafter in Example 2 for the preparation of N-formyl-N-methyl-2-phenylacetamide.

EXAMPLE 2

Preparation of N-methyl-2H-3-isoquinolone (known compound)

A solution of 80 g. N-formyl-N-methyl-2-phenyl-acetamide in 200 ml. concentrated sulfuric acid is left to stand for 12 hours at ambient temperature in an atmosphere of nitrogen. This solution is then poured, while stirring, into 1 liter ethanol and cooled in an ice bath in order to maintain the temperature at about 20°–30°C. The crystalline product obtained is filtered off and washed with cold ethanol and dried. There are obtained 70 g. N-methyl-2H-3-isoquinolone sulfate, which has a melting point of 235°–236°C.; yield 60% of theory. The analysis shows that it is a compound of the empirical formula $C_{10}H_9NO.H_2SO_4$:

analysis: calc. : C 46.6%; H 4.29%; N 5.45%; S 12.45%; found : C 46.9%; H 4.39%; N 5.40%; S 12.40%.

The product is perfectly stable whereas the free N-methyl-2H-3-isoquinolone is extremely easily oxidized (cf. N. J. Mruk and H. Tieckelmann, Tetrahedron Letters,14,(1970),1209–1212 and D. A. Evans et al., J.Chem.Soc. (B),1967,592).

The following procedure can be used for the liberation of the N-methyl-2H-3-isoquinolone:

70 g. N-methyl-2H-3-isoquinolone sulfate are dissolved, under an atmosphere of nitrogen, in 900 ml. water. 75 g. sodium bicarbonate are added and the mixture is stirred with 500 ml. chloroform. By decantation, there is obtained a chloroform solution of N-methyl-2H-3-isoquinolone, which can be dried over anhydrous sodium sulfate and employed as such or concentrated for a further reaction.

Because of the great oxidizability of N-methyl-2H-3-isoquinolone, it is, however, very advantageous to keep this product in the form of its sulfate and to liberate it only when desired.

Preparation of N-formyl-N-methyl-2-phenyl-acetamide (new compound)

To a solution of 59 g. (1 mol) monomethylformamide and of 79 g. (1 mol) pyridine in 200 ml. acetone, there is slowly added, at a temperature of about 0°C. and while stirring, a solution of 120 g. (0.77 mol) phenacetyl chloride in 200 ml. acetone. Stirring is continued in the cold for half an hour, followed by boiling under reflux for half an hour.

The reaction mixture is then evaporated to dryness and the residue is suspended in 500 ml. cold water. It is stirred and the product is filtered off, washed with water and recrystallized from diisopropyl ether. A second recrystallization from ethanol gives the pure product with a melting point of 65°–66°C. The yield is about 50% of theory.

However, it is not necessary to purify the crude N-formyl-N-methyl-2-phenyl-acetamide for the purpose of the cyclodehydration reaction. The product, separated after evaporation of the solvent and suspended in water, is filtered and dried. It may then be used directly for the reaction in concentrated sulfuric acid.

In this case, the yield of N-methyl-2H-3-isoquinolone, with a melting point of 235°–236°C., calculated upon the amount of phenacetyl chloride used, reaches 40–45%.

EXAMPLE 3

Preparation of 7-methyl-2H-3-isoquinolone (new compound)

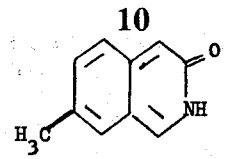

124 g. (0.7 mol) N-formyl-2-(p-methyl-phenyl)-acetamide in 400 ml. concentrated sulfuric acid is left to react for a period of 15 hours at ambient temperature in an atmosphere of nitrogen. The reaction mixture is then poured into a well stirred suspension, maintained at a temperature of about 20°C., of 1.2 kg. sodium bicarbonate in about 3.6 liters chloroform. The mixture is stirred for 1 hour, the mineral salts are then filtered off and the filtrate is successively washed with chloroform and methanol and the wash liquors are added to the filtrate. The filtrate is then evaporated to dryness and the residue is recrystallized from ethanol. The crystalline product obtained melts at 220°–222°C. The yield is 35% of theory.

analysis: $C_{10}H_9NO$ calc. : C 75.5%; H 5.66%; N 8.80%; found : C 76.0%; H 5.77%; N 8.89%.

The N-formyl-2-(p-methylphenyl)-acetamide (m.p. 144°–146°C.) used as starting material was prepared from formamide and 4-methyl-phenyl-acetyl chloride in the manner described in Example 2 for the preparation of N-formyl-N-methyl-2-phenyl-acetamide.

EXAMPLE 4

Preparation of 6,7-dimethoxy-N-methyl-2H-3-isoquinolone (known compound)

A solution of 6.55 g. (0.0276 mol) N-formyl-N-methyl-2-(3,4-dimethoxy-phenyl)-acetamide in 25 ml. concentrated sulfuric acid is left to stand for 16 hours, at ambient temperature, in an atmosphere of nitrogen.

This solution is then poured, dropwise, while stirring, into 150 ml. absolute ethanol. The crystalline product obtained is filtered off, washed with cold ethanol and dried. There are obtained 6.1 g. of the product, which melts at 258°–260°C.; yield 66% of theory.

The analysis shows that it is a compound of the formula $C_{12}H_{13}NO_3.H_2SO_4.H_2O$ analysis: calc. : C 42.9%; H 5.07%; N 4.18%; found : C 42.6%; H 5.06%; N 4.23%.

Preparation of N-formyl-N-methyl-2-(3,4-dimethoxy-phenyl)-acetamide. (new compound)

A solution of 35.5 g. (0.165 mol) homoveratric acid chloride (3,4-dimethoxyphenyl-acetic acid chloride) in 25 ml. acetone is slowly added, while stirring, at a temperature of 0°C., to a solution of 12.5 g. (0.33 mol) N-methylformamide and 13.2 g. (0.167 mol) pyridine in 50 ml. acetone. Stirring is continued in the cold for half an hour, followed by boiling under reflux for half an hour.

The reaction mixture is then evaporated to dryness and the residue is taken up in water and extracted twice with chloroform. The organic solution is dried over sodium sulfate and then distilled under a pressure of 0.005 mm. Hg. 31 g. of the product passing at a temperature between 160 and 166°C. are collected. This product is recrystallized from 30 ml. absolute ethanol. 23.2 g. of the desired product, having a melting point of 65°–66°C are obtained; yield: 59.2% of theory.

analysis: calc. : N 5.90%; found : N 5.91%.

Taking into account that the homoveratric acid chloride is obtained with a yield of 83%, the overall yield of 6,7-dimethoxy-N-methyl-2H-3-isoquinolone sulfate, in 3 steps, is 32%, which constitutes a considerable improvement as compared to the process of N. J. Mc Corkindale and A. W. Mc Culloch (4 steps and an overall yield of 13.3%).

EXAMPLE 5

The isoquinolones set out in the following Table I are new compounds which were prepared by one of the methods described in Examples 1 or 3. The yields obtained varied between 15 and 65%.

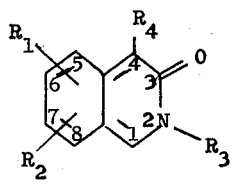

TABLE I

| $R_1$ | $R_2$ | $R_3$ | $R_4$ | M.P. °C. | Remarks |
|---|---|---|---|---|---|
| 5-$CH_3$ | H | H | H | 213–215 | |
| 5-$CH_3$ | H | $CH_3$ | H | 237–239 | (1) |
| 6-$CH_3$ | 8-$CH_3$ | H | H | 241–242 | |
| 6- and 8-$CH_3$ | H | H | H | 168–169 | (2) |
| 7-$C_2H_5$ | H | H | H | 149–150 | |
| 6- and 8-$C_2H_5$ | H | H | H | 122–142 | (2) |
| 6-$OCH_3$ | H | H | H | 205 | |
| 6-F | H | H | H | 229–230 | |
| 8-F | H | H | H | 128–130 | |
| 6-Cl | H | H | H | 250 | |
| 8-Cl | H | H | H | 221 | |
| H | H | n-$C_4H_9$ | H | 145 | (3) |
| H | H | $CH_2$—$C_6H_5$ | H | 135 | (4) |
| H | H | H | n-$C_4H_9$ | 137–139 | |
| H | H | H | $C_6H_5$ | 279–280 | (5) |

(1) Melting point of the sulfate.
(2) The products obtained are mixtures of the 6- and 8-isomers. Thus, the NMR spectrum of the 6- and 8-$CH_3$ product shows that it is a mixture containing about 60% of 8-$CH_3$ and 40% of 6-$CH_3$. In the case of the 6- and 8-ethyl mixture of isomers, this contains 65% of the 6-isomer and 35% of the 8-isomer. The 6-ethyl isomer has a m.p. of 238–241°C.
(3) Boiling point at a pressure of 0.01 mm.Hg. The product is not very stable but gives a readily crystallizable hydrochloride $C_{13}H_{15}NO.HCl$ which, after recrystallization from alcohol-ether, melts at 157–159°C.;
    Analysis: calc.  C 66.0%  H 6.4%  N 5.90%  $Cl^-$ 14.9%
    found :        65.6%   6.8%   5.63%  14.3%
(4) Melting point of the sulfate, crystallized from ethanol. $C_{16}H_{11}NO.H_2SO_4.H_2O$
    analysis: calc. :  C 55.0%  H 4.3%  N 4.1%  $H_2O$ 5.1%
    found :        55.8%   4.5%   3.9%     4.9%
(5) This compound is known.

These 2H-3-isoquinolones were obtained from the following N-formyl-2-phenyl-acetamides, prepared in the manner described in Examples 2 and 4:

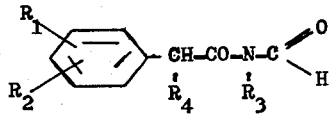

TABLE II

| $R_1$ | $R_2$ | $R_3$ | $R_4$ | M.P. °C. | |
|---|---|---|---|---|---|
| 2-$CH_3$ | H | H | H | 142–143 | |
| 2-$CH_3$ | H | $CH_3$ | H | 62–63 | |
| 3-$CH_3$ | 5-$CH_3$ | H | H | 151–152 | |
| 3-$CH_3$ | H | H | H | 112–113 | |
| 4-$C_2H_5$ | H | H | H | 120–122 | |
| 3-$C_2H_5$ | H | H | H | 85–86 | |
| 3-$OCH_3$ | H | H | H | 101–102 | |
| 3-F | H | H | H | 120–121 | |
| 3-Cl | H | H | H | 143–145 | |
| H | H | n—$C_4H_9$ | H | 130 | (x) |
| H | H | $CH_2$—$C_6H_5$ | H | 145 | (x) |
| H | H | H | n—$C_4H_9$ | 66–67 | |
| H | H | H | $C_6H_5$ | 175–177 | |

(x) Boiling point at 0.01 mm.Hg.

All the above compounds are new; the yields obtained are of the order of 30 to 65%.

We claim:

1. A process for the preparation of 2H-3-isoquinolone having the formula

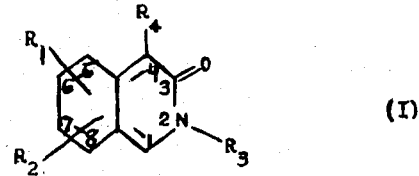

wherein $R_1$ represents a member selected from the group consisting of hydrogen, chlorine, fluorine, alkyl having 1 to 6 carbon atoms and alkoxy having 1 to 6 carbon atoms, $R_2$ represents a member selected from the group consisting of hydrogen and alkyl having 1 to 6 carbon atoms, and
$R_3$ and $R_4$ each represent a member selected from the group consisting of hydrogen, alkyl having 1 to 6 carbon atoms, alkenyl having 2 to 6 carbon atoms, phenyl, naphthyl, tolyl, xylyl, benzyl and phenethyl,
which comprises treating an N-formyl-2-phenylacetamide of the formula

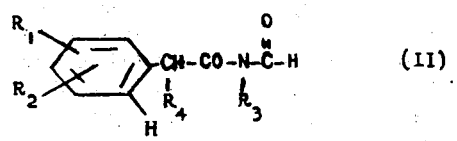

wherein $R_1$, $R_2$, $R_3$ and $R_4$ have the same meanings as above, with sulfuric acid at a temperature between 0° and 60°C to cyclize the acetamide compound.

2. The process of claim 1, wherein the 2H-3-isoquinolone of obtained as the sulfuric acid addition salt is converted into the free base by addition of a base in an amount sufficient to release the free base from said sulfuric addition salt.

3. The process of claim 1, wherein 2H-3-isoquinolone is prepared by cyclizing N-formyl-2-phenyl-acetamide.

4. The process of claim 1, wherein N-methyl-2H-3-isoquinolone is prepared by cyclizing N-formyl-N-methyl-2-phenyl-acetamide.

5. The process of claim 1, wherein 7-methyl-2H-3-isoquinolone is prepared by cyclizing N-formyl-2-(p-methyl-phenyl)-acetamide.

6. The process of claim 1, wherein 2,5-dimethyl-2H-3-isoquinolone is prepared by cyclizing N-formyl-N-methyl-2-(o-methyl-phenyl)-acetamide.

7. The process of claim 1, wherein 6,8-dimethyl-2H-3-isoquinolone is prepared by cyclizing N-formyl-2-(3,5-dimethyl-phenyl)-acetamide.

8. The process of claim 1, wherein 7-ethyl-2H-3-isoquinolone is prepared by cyclizing N-formyl-2-(p-ethyl-phenyl)-acetamide.

9. The process of claim 1, wherein 6-methoxy-2H-3-isoquinolone is prepared by cyclizing N-formyl-2-(m-methoxy-phenyl)-acetamide.

10. The process of claim 1, wherein 6-fluoro-2H-3-isoquinolone is prepared by cyclizing N-formyl-2-(m-fluoro-phenyl)-acetamide.

11. The process of claim 1, wherein 8-chloro-2H-3-isoquinolone is prepared by cyclizing N-formyl-2-(m-chloro-phenyl)-acetamide.

12. The process of claim 1, wherein N-n-butyl-2H-3-isoquinolone is prepared by cyclizing N-formyl-N-n-butyl-2-phenyl-acetamide.

13. The process of claim 1, wherein N-benzyl-2H-3-isoquinolone is prepared by cyclizing N-formyl-N-benzyl-2-phenyl-acetamide.

14. The process of claim 1, wherein 4-n-butyl-2H-3-isoquinolone is prepared by cyclizing N-formyl-2-n-butyl-2-phenyl-acetamide.

* * * * *